United States Patent
Lee et al.

(10) Patent No.: US 11,733,161 B2
(45) Date of Patent: Aug. 22, 2023

(54) METHOD OF DETERMINING CONCENTRATION OF SUBJECT BASED ON FRACTION BOUND MEASUREMENT

(71) Applicant: Korea Advanced Institute of Science and Technology, Daejeon (KR)

(72) Inventors: Hansuek Lee, Daejeon (KR); Yeseul Kim, Daejeon (KR)

(*) Notice: Subject to any disclaimer, the term of this patent is extended or adjusted under 35 U.S.C. 154(b) by 2 days.

(21) Appl. No.: 16/907,728

(22) Filed: Jun. 22, 2020

(65) Prior Publication Data
US 2021/0109096 A1    Apr. 15, 2021

(30) Foreign Application Priority Data

Oct. 11, 2019 (KR) .................. 10-2019-0125916

(51) Int. Cl.
*G01N 21/552* (2014.01)
*G01N 21/76* (2006.01)
(Continued)

(52) U.S. Cl.
CPC ......... *G01N 21/553* (2013.01); *G01N 21/554* (2013.01); *G01N 21/76* (2013.01); *G01N 21/77* (2013.01); *G01N 33/53* (2013.01); *G01N 2021/7789* (2013.01); *G01N 2201/062* (2013.01)

(58) Field of Classification Search
CPC .......... G01N 33/54386; G01N 21/553; G01N 21/554; G01N 21/76; G01N 21/77; G01N 33/53; G01N 2021/7789; G01N 2201/062; G01N 21/658
See application file for complete search history.

(56) References Cited

U.S. PATENT DOCUMENTS

| 6,632,613 B1* | 10/2003 | Wei .................. G01N 33/54373 435/7.1 |
| 2003/0162236 A1* | 8/2003 | Harris .................. G01N 33/558 435/7.92 |

(Continued)

FOREIGN PATENT DOCUMENTS

| KR | 100480340 B1 | 3/2005 | |
| WO | WO-2007071349 A1 * | 6/2007 | ......... G01N 21/6428 |

OTHER PUBLICATIONS

Kim et al., "Luminescent Silicon-Rich Nitride Horizontal Air-Slot Microdisk Resonators for Biosensing", 2016, IEEE Photonics Technology Letters, vol. 28, No. 21 (Year: 2016).*

(Continued)

*Primary Examiner* — Samuel P Siefke
*Assistant Examiner* — Henry H Nguyen
(74) *Attorney, Agent, or Firm* — KDW Firm PLLC

(57) ABSTRACT

Disclosed herein is a method of determining a concentration of a subject based on fraction bound measurement. The method of determining a concentration of a subject based on fraction bound measurement may include fixing a ligand to a surface of an optical device, measuring a fraction bound of a subject to be detected based on an optical signal when the subject reacts to the ligand fixed to the surface of the optical device, and determining a relative value of a concentration of the subject based on a ratio of measured values of the fraction bounds of the subject and a reference signal.

8 Claims, 21 Drawing Sheets

(51) Int. Cl.
*G01N 21/77* (2006.01)
*G01N 33/53* (2006.01)

(56) References Cited

U.S. PATENT DOCUMENTS

| | | | | |
|---|---|---|---|---|
| 2004/0029293 A1* | 2/2004 | Nugent | ................... | B01L 9/52 |
| | | | | 435/287.2 |
| 2007/0172906 A1 | 7/2007 | Valkirs et al. | | |
| 2009/0261269 A1* | 10/2009 | Horii | ................... | G01N 21/05 |
| | | | | 250/459.1 |
| 2012/0244554 A1* | 9/2012 | Giavazzi | .......... | G01N 33/54313 |
| | | | | 435/7.4 |
| 2014/0227720 A1* | 8/2014 | Wilson | ............. | G01N 33/57434 |
| | | | | 435/7.92 |
| 2015/0247846 A1* | 9/2015 | Gerion | ................ | G01N 21/554 |
| | | | | 506/9 |

OTHER PUBLICATIONS

Vollmer et al., "Whispering-gallery-mode biosensing: label-free detection down to single molecules", 2008, Nature Methods, 5, 591-596 (Year: 2008).*

Taniguchi et al., "Detection of antibody-antigen reaction by silicon nitride slot-ring biosensors using protein G", 2016, Optics Communications, 365, pp. 16-23 (Year: 2016).*

Kim, et al., "Towards next-generation label-free biosensors: recent advances in whispering gallery mode sensors", Lab on a Chip, vol. 17, No. 7, Apr. 2017, pp. 1190-1205.

* cited by examiner

METHOD OF DETERMINING CONCENTRATION OF SUBJECT BASED ON FRACTION BOUND MEASUREMENT

CROSS REFERENCE TO RELATED APPLICATION

This application is based on and claims priority under 35 U.S.C. 119 to Korean Patent Application No. 10-2019-0125916, filed on Oct. 11, 2019, in the Korean Intellectual Property Office, the disclosures of which is herein incorporated by reference in their entireties.

BACKGROUND OF THE INVENTION

Field of the Invention

The following embodiments relate to a method of determining a concentration of a subject and, more particularly, to a method of determining a concentration of a subject based on fraction bound measurement.

Related Art

The measurement of the concentration of a subject based on fraction bound measurement is a scheme being actively used in various fields. For example, in a surface plasmon resonance resonator or a whispering gallery mode (WGM) resonator being actively researched as optical sensors, after a ligand is fixed to a surface of an optical device, when a subject to be detected reacts to the ligand fixed to the surface, the concentration and dynamic characteristic of the subject are analyzed using a fraction bound based on an optical signal measured through the reaction.

The existing method of determining a concentration based on fraction bound measurement adopts a method of reacting, with ligands, a reference sample whose concentration is already known and a sample whose concentration is to be known, respectively, and determining a relative concentration by comparing initial reaction velocities through separate measurements.

In the existing method of determining a concentration based on fraction bound measurement, however, a concentration can be determined only when the measurement of a signal at the initial step of a reaction is successful. The determination of the concentration is impossible if corresponding timing is missed. At the initial step of a reaction, it is difficult to measure a concentration due to the arrangement of an optical part or device for measurement.

Furthermore, since a concentration is determined by relatively comparing a sample signal with a reference signal through separate measurements, various external factors affecting the measurement have an effect on the accuracy of each signal. It is difficult to control the influence.

A sensor based on a whispering gallery mode (WGM) resonator has been widely researched in relation to detection not having the label of biological/chemical molecules for the past 10 years. In this case, the WGM refers to a specific resonance mode contained within a resonator having a smooth edge, such a sphere or disk, due to continuous and internal total reflection. In the sensor, a detection event is monitored based on a change in the WGM resonant frequency which occurs as the length of the optical path of a photon circulating in the resonator is increased when a specific molecule is combined with a surface. Such a technology has proved a great potential power in analysis on the dynamics of molecules based on the real-time measurement of an interaction between specific biomolecules, which may be precisely solved based on high-quality factors and a small mode volume of the resonator. Furthermore, there is a possibility that the resonator, that is, a core part for detection, may be implemented in a small detection device of a chip because the resonator has a micro size. Despite such an advantage of the WGM-based sensor, most of WGM-based sensor experiments are limited to academic studies and a substantial influence on the outside of a laboratory is very small so far.

A fundamental limit to hinder the development of a practical WGM sensor device chiefly results from a light coupling method based on evanescent coupling in which a waveguide must have proper physical dimensions in order to satisfy a phase matching condition. For proper connection efficiency, there is a need for a precise method capable of controlling a gap between the waveguide and a nanoscale resonator. Furthermore, a tapered optical fiber, that is, a waveguide commonly used for coupling, is unstable mechanically, and has a difficulty in being combined with a microfluidic channel. In contrast, a bus waveguide uniformly implemented in a resonator chip is very robust, but requires significant micro manufacture precision in order to control the gap and additional efforts for implementing proper optical coupling at the end of the waveguide, such as end-fire coupling.

In order to overcome such a limit, the concept of a WGM sensor based on an optical active resonator has emerged as a promising alternative. In this approach method, a pump light exposed at the top of the optical active resonator induces an emission spectrum peak along with a resonance mode, which is detected by a spectrometer through a free space optical system. A sensor system can be significantly simplified in a practical form because a direct physical contact for driving an optical device is not necessary. The detection of a specific molecule has recently been proved in a chip integrated with a fusion channel based on the approach method. A polymer microcavity doped with laser dyes is used in the active resonator. However, the active resonator needs to be pumped using a high pulse laser (86 nJ/pulse), and sensitivity thereof is maintained lower than common sensitivity expected in the WGM resonator sensor. As another approach method for the optically active WGM-based resonator, a silicon-rich silicon nitride (SRSN) microcavity in which a silicon nano-clusters functions as an active compound was proposed. The detection of a molecule in the air was proved based on the microcavity, but an actual sensor platform integrated with a microfluidic channel and the real-time detection of a specific molecule based on the actual sensor platform has not yet been proved.

Additional background discussion may be found in Eugene Kim, Martin D Baaske, and Frank Vollmer, "Towards next-generation label-free biosensors: recent advances in whispering gallery mode sensors," Lab on a Chip, 17(7):1190-1205, 2017, the entire disclosure of which is incorporated herein by reference.

It is with the above considerations in mind that the improvements of the present disclosure may be useful.

SUMMARY OF THE INVENTION

Embodiments are related to a method of determining a concentration of a subject based on fraction bound measurement and, more particularly, providing a fast and efficient technology capable of determining a relative concentration of a sample based on a comparison with a reference signal through only one signal measurement at any reaction timing in addition to an initial stage.

Furthermore, embodiments provide a method of determining a concentration of a subject based on fraction bound measurement, which enables accurate measurement by offsetting an external factor that may affect experiment results through the simultaneous measurement of a reference signal and a sample signal.

In an embodiment, a method of determining a concentration of a subject based on fraction bound measurement may include fixing a ligand to a surface of an optical device, measuring a fraction bound of a subject to be detected based on an optical signal when the subject reacts to the ligand fixed to the surface of the optical device, and determining a relative value of a concentration of the subject based on a ratio of measured values of the fraction bounds of the subject and a reference signal.

Measuring the fraction bound of the subject based on the optical signal may include measuring the fraction bound of the subject indicative of the number of ligands combined with the subject against a total number of the ligands.

Measuring the fraction bound of the subject based on the optical signal may include analyzing the fraction bound through a Langmuir model in an environment in which the ligand has been fixed to the surface of the optical device.

Determining a relative value of a concentration of the subject may include determining the relative value of the concentration of the subject based on a ratio of measured values of fraction bounds of the subject and reference signal defined in each step of the reaction when the subject reacts to the ligand fixed to the surface of the optical device.

Determining a relative value of a concentration of the subject may include determining the relative value of the concentration of the subject based on a ratio of measured values of fraction bounds of the subject and reference signal defined in an initial step, intermediate step and saturation step of the reaction.

In determining the relative value of the concentration of the subject, the ratio of the measured values of the fraction bounds of the subject and reference signal in the intermediate step may have a middle value between the ratio of the measured values of the fraction bounds of the subject and reference signal in the initial step and the ratio of the measured values of the fraction bounds of the subject and reference signal in the saturation step.

In determining a relative value of a concentration of the subject, the relative concentration of the subject may be determined based on a comparison with the reference signal through only one signal measurement at any reaction timing by determining the relative value of the concentration of the subject based on the ratio of the measured values of the fraction bounds of the subject and reference signal.

Measuring a fraction bound of the subject based on the optical signal may include measuring the fraction bound of the reference signal and measuring the fraction bound of the subject.

Measuring a fraction bound of the subject based on the optical signal may include simultaneously measuring the fraction bound of the reference signal and the fraction bound of the subject in such a way as to enable accurate measurement by offsetting external factors capable of affecting experiments.

Measuring the fraction bound of the subject based on the optical signal may include simultaneously measuring signals of a plurality of samples in an identical condition in such a way as to enable accurate measurement by offsetting external factors which may affect experiments.

The method further includes fabricating an optical active resonator used as the optical device in the fraction bound measurement. Fabricating the optical active resonator may include forming silicon nano-clusters within a plurality of silicon nitride disk plates and disposing the plurality of silicon nitride disk plates in such a way as to be spaced apart from each other at a given interval to form a nano-slot. Photoluminescence (PL) may be emitted by only top pump beam radiation through absorption cross sections of the silicon nano-clusters.

The method further includes radiating a pump beam of a single light-emitting diode (LED) over the optical active resonator for the fraction bound measurement. The PL may be emitted by only top pump beam radiation of the single LED through the absorption cross sections of the silicon nano-clusters.

In another embodiment, an apparatus for determining a concentration of a subject based on fraction bound measurement may include a setup unit configured to fix a ligand to a surface of an optical device, a fraction bound measurement unit configured to measure a fraction bound of a subject to be detected based on an optical signal when the subject reacts to the ligand fixed to the surface of the optical device, and a concentration determination unit configured to determine a relative value of a concentration of the subject based on a ratio of measured values of the fraction bounds of the subject and a reference signal.

The fraction bound measurement unit may measure the fraction bound of the subject indicative of the number of ligands combined with the subject against a total number of the ligands.

The fraction bound measurement unit may analyze the fraction bound through a Langmuir model in an environment in which the ligand may have been fixed to the surface of the optical device.

The concentration determination unit may determine the relative value of the concentration of the subject based on a ratio of measured values of fraction bounds of the subject and reference signal defined in each step of the reaction when the subject reacts to the ligand fixed to the surface of the optical device.

The concentration determination unit may determine the relative value of the concentration of the subject based on a ratio of measured values of fraction bounds of the subject and reference signal defined in an initial step, intermediate step and saturation step of the reaction. The ratio of the measured values of the fraction bounds of the subject and reference signal in the intermediate step may have a middle value between the ratio of the measured values of the fraction bounds of the subject and reference signal in the initial step and the ratio of the measured values of the fraction bounds of the subject and reference signal in the saturation step.

The concentration determination unit may determine the relative concentration of the subject based on a comparison with the reference signal through only one signal measurement at any reaction timing by determining the relative value of the concentration of the subject based on the ratio of the measured values of the fraction bounds of the subject and reference signal.

The fraction bound measurement unit simultaneously may measure the fraction bound of the reference signal and the fraction bound of the subject in such a way as to enable accurate measurement by offsetting external factors which may affect experiments.

DESCRIPTION OF EXEMPLARY EMBODIMENTS

Figure 1A:
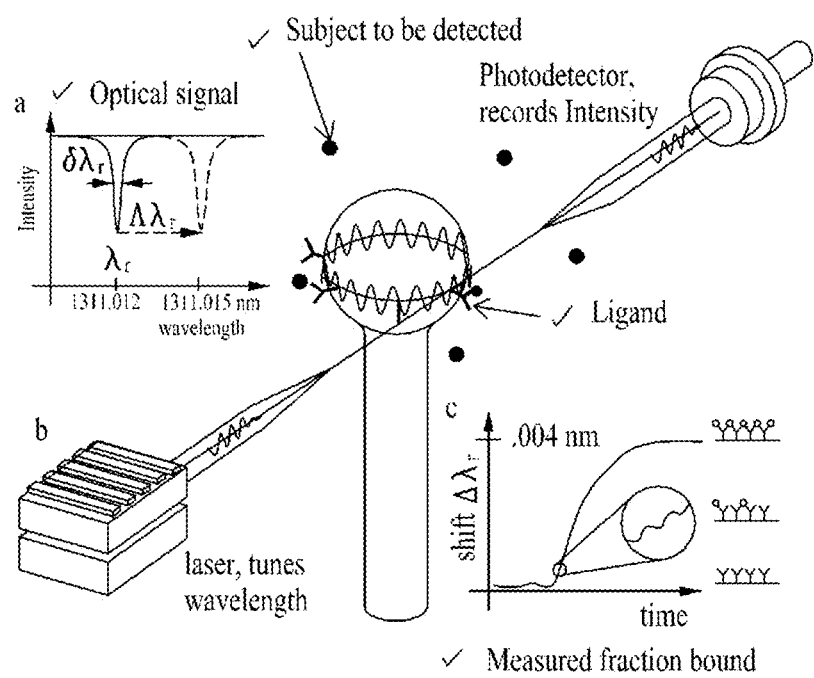
FIG. 1A illustrates an example of a fraction bound measurement method based on an optical resonator according to an embodiment.

Hereinafter, embodiments are described in detail with reference to the accompanying drawings. However, the described embodiments may be modified in various other forms, and the scope of the present disclosure is not restricted by the following embodiments. Furthermore, the embodiments of the present disclosure are provided to fully describe the present disclosure to a person having ordinary knowledge in the art to which the present disclosure pertains. The shapes, sizes, etc. of elements in the drawings may be exaggerated for a clear description.

The following embodiments relate to a method of determining a concentration of a subject based on fraction bound measurement, and provide a fast and efficient method capable of determining a relative concentration of a sample. If the method is used, a concentration can be determined based on a comparison with a reference signal through only one signal measurement at any reaction timing in addition to an initial stage. Furthermore, the following embodiments provide a method capable of accurately measuring a concentration by offsetting an external factor which may affect experiment results through the simultaneous measurement of a reference signal and a sample signal.

Figure 1B:
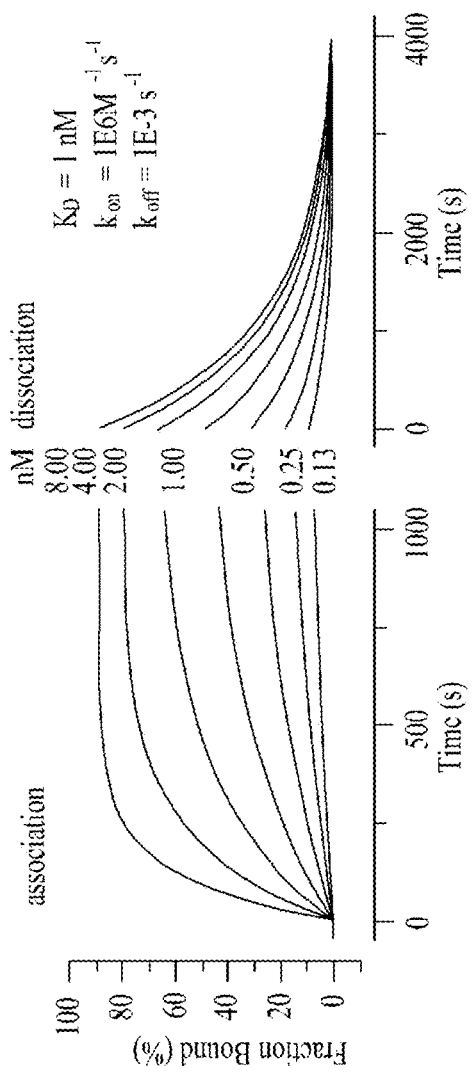
FIG. 1B illustrates an example of a fraction bound signal measured for each concentration according to an embodiment.

FIG. 1A illustrates an example of a fraction bound measurement method based on an optical resonator. FIG. 1B illustrates an example of a fraction bound signal measured for each concentration.

As illustrated in FIG. 1A, after a ligand is fixed to a surface of an optical device such as a photodetector, when a subject to be detected reacts to the ligand fixed to the surface, a fraction bound based on an optical signal may be measured as illustrated in FIG. 1B. Furthermore, a concentration and dynamic characteristic of the subject may be analyzed using the measured fraction bound based on the optical signal. In this case, a surface plasmon resonance resonator or a whispering gallery mode (WGM) resonator may be used as the optical device.

Figure 2:
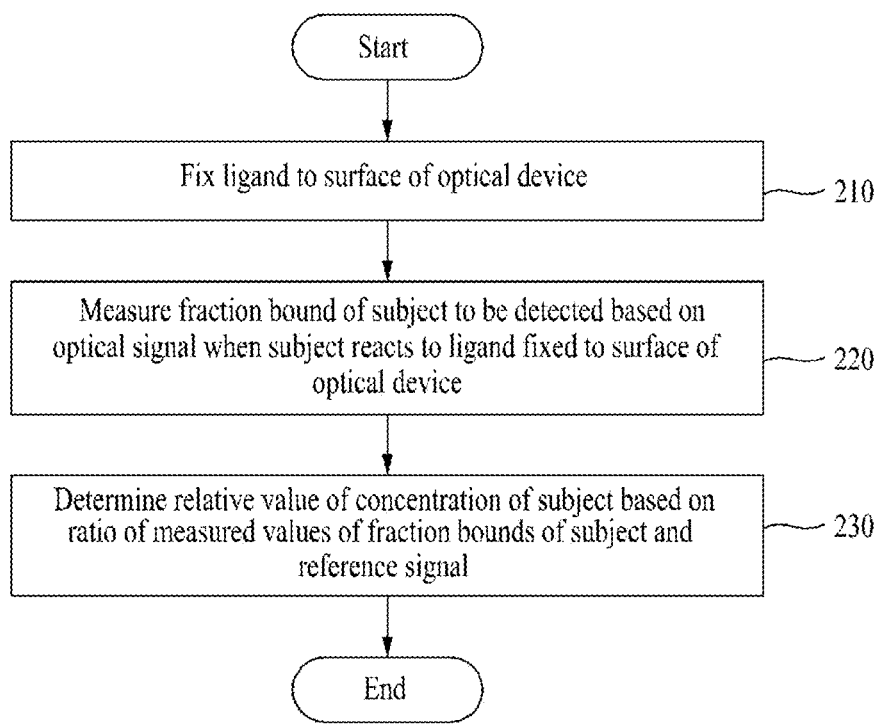
FIG. 2 is a flowchart illustrating a method of determining a concentration of a subject based on fraction bound measurement according to an embodiment.

FIG. 2 is a flowchart illustrating a method of determining a concentration of a subject based on fraction bound measurement according to an embodiment.

Referring to FIG. 2, the method of determining a concentration of a subject based on fraction bound measurement according to an embodiment may include the step 210 of fixing a ligand to a surface of an optical device, the step 220 of measuring a fraction bound of a subject to be detected based on an optical signal when the subject reacts to the ligand fixed to the surface of the optical device, and the step 230 of determining a relative value of a concentration of the subject based on the ratio of measured values of the fraction bounds of the subject and a reference signal.

In some embodiments, the method of determining a concentration of a subject based on fraction bound measurement may further include the step of fabricating an optical active resonator used as the optical device in the fraction bound measurement. Furthermore, the method may further include the step of radiating the pump beam of a single LED over an optical active resonator for the fraction bound measurement.

A method of determining a concentration of a subject based on fraction bound measurement is described more specifically below.

The method of determining a concentration of a subject based on fraction bound measurement may be described more specifically by taking an apparatus for determining a concentration of a subject based on fraction bound measurement as an example.

Figure 3:
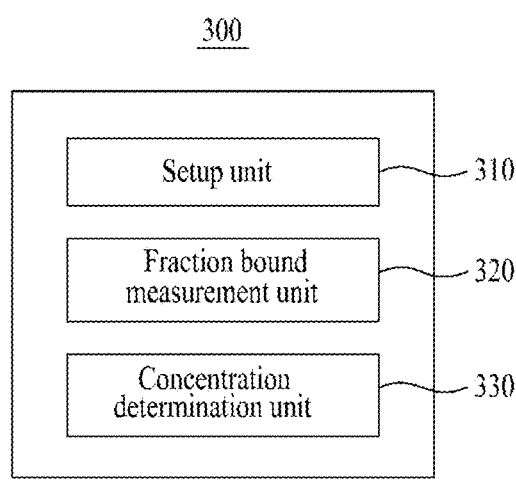
FIG. 3 is a block diagram illustrating an apparatus for determining a concentration of a subject based on fraction bound measurement according to an embodiment.

FIG. 3 is a block diagram illustrating an apparatus 300 for determining a concentration of a subject based on fraction bound measurement according to an embodiment.

Referring to FIG. 3, the apparatus 300 for determining a concentration of a subject based on fraction bound measurement according to an embodiment may include a setup unit 310, a fraction bound measurement unit 320 and a concentration determination unit 330. In some embodiments, the apparatus may further include an optical active resonator fabrication unit and a light emitting diode (LED) radiation unit.

At step 210, the setup unit 310 may fix a ligand to a surface of an optical device. In this case, a photodetector, such as a surface plasmon resonance resonator or a WGM resonator, may be used as the optical device. Particularly, the optical device may be an optical active resonator. The optical active resonator may include a silicon nitride disk plate and a silicon nano-clusters, and may further include a nano-slot. Such an optical active resonator is described in detail below.

At step 220, when the subject to be detected reacts to the ligand fixed to the surface of the optical device, the fraction bound measurement unit 320 may measure a fraction bound of the subject based on an optical signal. The fraction bound measurement unit 320 may measure the fraction bound of the subject, indicating the number of ligands combined with the subject against a total number of ligands. In this case, the fraction bound measurement unit 320 may analyze the fraction bound of the subject through a Langmuir model in an environment in which the ligand has been fixed to the surface of the optical device.

A method of measuring a concentration based on a ratio of a reference signal and a sample signal is described more specifically. In this case, the sample signal may mean a fraction bound measurement signal of a subject.

Detection (e.g., using a known photodetector) performed in an environment in which a ligand has been fixed to a surface of an optical device may be analyzed through the Langmuir model. In the Langmuir model, a fraction bound "fb" is a value proportional to a signal and may be represented as in the following equation.

$$\text{Fraction bound "} fb \text{"} = \frac{\text{Number of ligands combined with subject}}{\text{Total number of ligands}} \quad (1)$$

Furthermore, the fraction bound may be represented as the following equation.

$fb(t,c) = fbeq(c) \times [1 - \exp(-k_{on}^{obs} \cdot t)]$: measured value of photodetector t: time
c: concentration $$fbeq(c) = \frac{c}{c + Kd} \text{ (signal in equilibrium state)} \quad (2)$$

$$k_{on}^{obs} = C \cdot k_{on} + k_{off}$$

The step of measuring, by the fraction bound measurement unit 320, the fraction bound of the subject based on the optical signal may include the step of measuring a fraction bound of a reference signal and the step of measuring a fraction bound of the subject. In this case, the fraction bound measurement unit 320 may measure the fraction bound of the reference signal and the fraction bound of the subject at the same time in such a way as to enable accurate measurement by offsetting external factors which may affect experiments. Furthermore, the fraction bound measurement unit 320 may measure signals of a plurality of samples at the same time in the same condition in such a way as to enable accurate measurement by offsetting external factors which may affect experiments.

In a platform capable of the simultaneous measurement of the fraction bounds of a reference sample and a detection sample, signals of several samples may be measured at the same time in the same condition. As a result, external factors (e.g., temperature change and pre-processing state) which may affect experiments can be offset, and more accurate measurement is possible. This has an effect in that a signal is filtered by offsetting common noise in a differential amplifier.

At step 230, the concentration determination unit 330 may determine a relative value of the concentration of the subject based on the ratio of measured values of the fraction bounds of the subject and the reference signal. More specifically, when the subject reacts to the ligand fixed to the surface of the optical device, the concentration determination unit 330 may determine a relative value of the concentration of the subject based on the ratio of measured values of the fraction bounds of the subject and reference signal defined in each step of the reaction. For example, the concentration determination unit 330 may determine a relative value of the concentration of the subject based on the ratio of measured values of the fraction bounds of the subject and reference signal defined in each of the initial step, intermediate step and saturation step of the reaction. In this case, the ratio of measured values of the fraction bounds of the subject and reference signal in the intermediate step may have a middle value between the ratio of measured values of the fraction bounds of the subject and reference signal in the initial step and the ratio of measured values of the fraction bounds of the subject and reference signal in the saturation step.

When the concentration determination unit 330 determines a relative value of the concentration of the subject based on the ratio of measured values of the fraction bounds of the subject and reference signal as described above, the concentration determination unit 330 can determine a relative concentration of the subject based on a comparison with the reference signal through only one signal measurement at any reaction timing.

The ratio of the reference signal and the sample signal may be defined as R(t), and may be represented as in the following equation.

$$R(t) = \frac{fb(t, C_{sample})}{fb(t, C_{reference})}: \text{Ratio of measured} \quad (3)$$

values of reference signal and sample signal

In each step of the reaction, R(t) may be defined as follows.

First, in the initial step (or initial state), R(t) may be defined as in the following equation.

$$R(t) = \frac{fb(0, C_{sample})}{fb(0, C_{reference})} = \frac{fb'(0, C_{sample})}{fb'(0, C_{reference})} = \frac{C_{sample}}{C_{reference}} \quad (4)$$

Furthermore, in the saturation step (or saturation state), R(t) may be defined as in the following equation.

$$R(t) = \frac{C_{sample} * (C_{reference} + K_d)}{C_{reference} * (C_{sample} + K_d)} \quad (5)$$

Furthermore, in the intermediate step (or intermediate state), R(t) may be defined as in the following equation.

$$\frac{C_{sample}}{C_{reference}} \approx \frac{fb(t, C_{sample})}{fb(t, C_{reference})}(= R(t)) \quad (6)$$

In this case, R(t) has a middle value between R(t) in the initial state and R(t) in the saturation state. The reason for this is that R(t) is a monotone function (R'(t)<0 or R'(t)>0)

As a result, a relative value of the concentration can be determined based on the value R(t). That is, the concentration can be determined based on a comparison between the signals through one measurement at any timing. Furthermore, an error rate can be determined based on the determined concentration through an error rate graph.

As described above, the method proposed through embodiments is fast and efficient because a concentration can be determined through one measurement. According to embodiments, a concentration can be determined at any time without being limited to reaction timing. A measured error rate can also be determined based on the measured concentration. Accordingly, an experiment design for more accurate concentration measurement is possible. Furthermore, a reference sample and a subject sample signal can be measured at the same time. Accordingly, more accurate measurement is possible because a change attributable to external factors (e.g., temperature change and pre-processing state) which may affect a measured signal can be offset.

In some embodiments, the apparatus may further include the optical active resonator fabrication unit and the LED radiation unit.

The optical active resonator fabrication unit may fabricate an optical active resonator used as an optical device in fraction bound measurement. The step of fabricating, by the optical active resonator fabrication unit, an optical active resonator includes the step of forming silicon nano-clusters within a plurality of silicon nitride disk plates and a step in which the plurality of silicon nitride disk plates are spaced apart from each other at a given interval to form nano-slots. PL can be emitted by only top pump beam radiation through an absorption cross section of the silicon nano-clusters.

Furthermore, the LED radiation unit may radiate the pump beam of a single LED over the optical active resonator for fraction bound measurement. Accordingly, PL can be emitted by only the top pump beam radiation of the single LED through the absorption cross section of the silicon nano-clusters.

Furthermore, the nano-slot can focus a resonance mode within the optical active resonator, and may be filled with a medium including a material to be detected, which has a lower refractive index than the silicon nitride disk plate. This is described in detail below.

An optical resonator-based sensor has a high quality factor and high sensitivity because it has a simple structure and can contain light within the resonator for a long time. As a result, the sensor has an advantage in that it has a low limit of detection, that is, a quantitative index of sensor performance. The optical resonator-based sensor can perform detection without labeling which may cause physical or chemical distortion because the detection is performed according to a mechanism based on an interaction between light and a subject. Furthermore, the optical resonator-based sensor can monitor whether a material is present and a change of a concentration in real time. A signal measured by the sensor can be converted into an electronic signal.

Owing to such advantage, research related to the optical resonator-based sensor continues for the past ten years. However, such research practically remains in research of an idea verification level based on complicated experiment setup, such as an expensive laser, in a limited environment such as a laboratory. The clinical utilization and commercialization of the research are some way off.

Although a high-performance optical device has been developed and a technology therefor has been accumulated to the extent that whether a single protein is present can be measured through active research into the optical resonator-based sensor as described above, the existing research has been considered as being a technology inappropriate for being used in an actual clinical environment because it has great complexity. A major cause may include the evanescent field coupling system of the optical resonator. The evanescent field coupling system is expensive, requires a wavelength-variable laser having a large volume, and also requires an optical waveguide for optically coupling laser light into the optical resonator.

A nanooptical fiber is an optical waveguide commonly used in such applications. The nanooptical fiber can perform optical coupling by only control of a location of several tens of nanometers based on expensive equipment, such as a piezo stage. Furthermore, an optical coupling system based on a nanooptical fiber becomes a major cause to make impossible an on-chip device implementation because mechanical coupling with a microfluidic channel is difficult in terms of its structure. Such a technology is a complex technology which may be implemented by only a skilled researcher in a limited laboratory environment. For this reason, clinical utilization and commercialization for the optical coupling system are impossible.

The following embodiments relate to an on-chip sensor device in which an optical active resonator and a microfluidic channel have been combined and a method of fabricating the same, and may provide a whispering gallery mode (WGM) sensor not having labeling, which has been integrated with a microfluidic channel based on an optically active silicon-rich silicon nitride (SRSN) resonator having a nano-slot structure. A measurement system in which emission, remote pumping and reading are performed in a connector for a direct physical contact point, such as a tapered fiber, through very efficient light discharge occurring in a silicon nanostructure can be simplified. A proper operation of the developed sensor was limited by real-time measurement for molecule bonding dynamics of a streptavidin-biotin complex that shows a connection ratio of $3 \times 10^{-4} M^{-1} s^{-1}$ and a separation constant of 380 nM corresponding to previously reported values. An interaction between light and a material has been improved in the nano-slot structure. Accordingly, 0.012 nm/nM, that is, improved sensitivity of 20 times or more, can be proved through real-time measurement of the streptavidin-biotin complex using the WGM sensor capable of remote reading. Furthermore, the concentration of a material to be analyzed can be determined with substantially necessary accuracy through a comparison with a concentration reference known as a single measurement using a newly proposed detection method similar to balanced detection. Furthermore, in this case, setup complexity and a cost can be significantly reduced by providing the detection of a whispering gallery mode (WGM) using an LED as a pump source for the first time.

A photodetector for fraction bound measurement and a method of fabricating the same are described below.

Figure 4A:
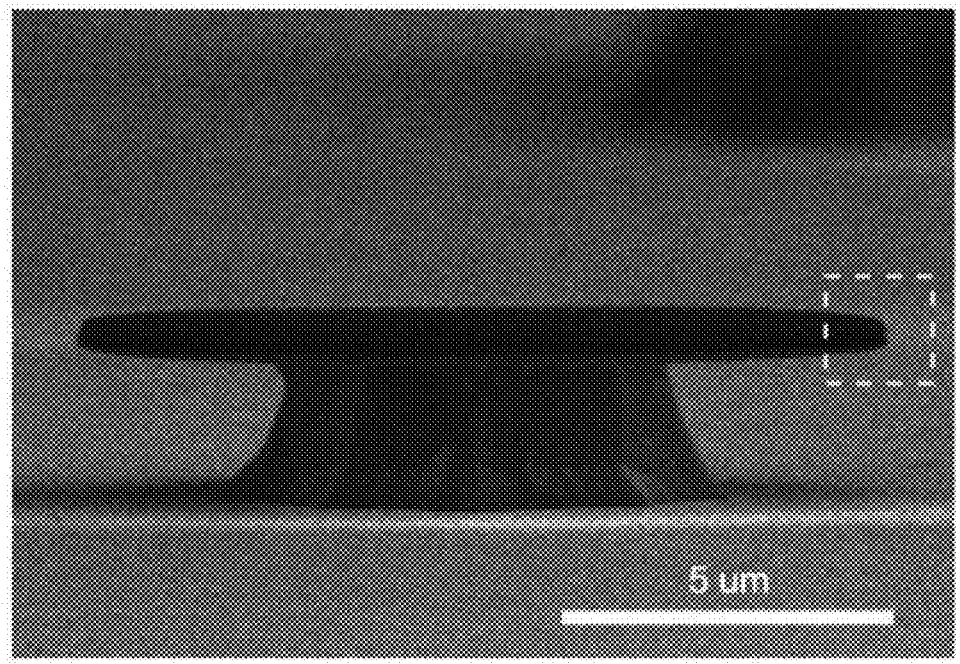
FIG. 4A illustrates an image of the scanning electron microscope (SEM) of a 12 μm disk resonator according to an embodiment.
Figure 4B:
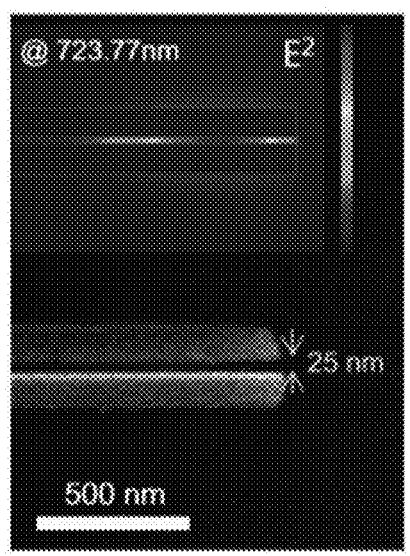
FIG. 4B is a partially enlarged view of FIG. 4A and illustrates two disks and a 25 nm slot according to an embodiment.
Figure 4C:
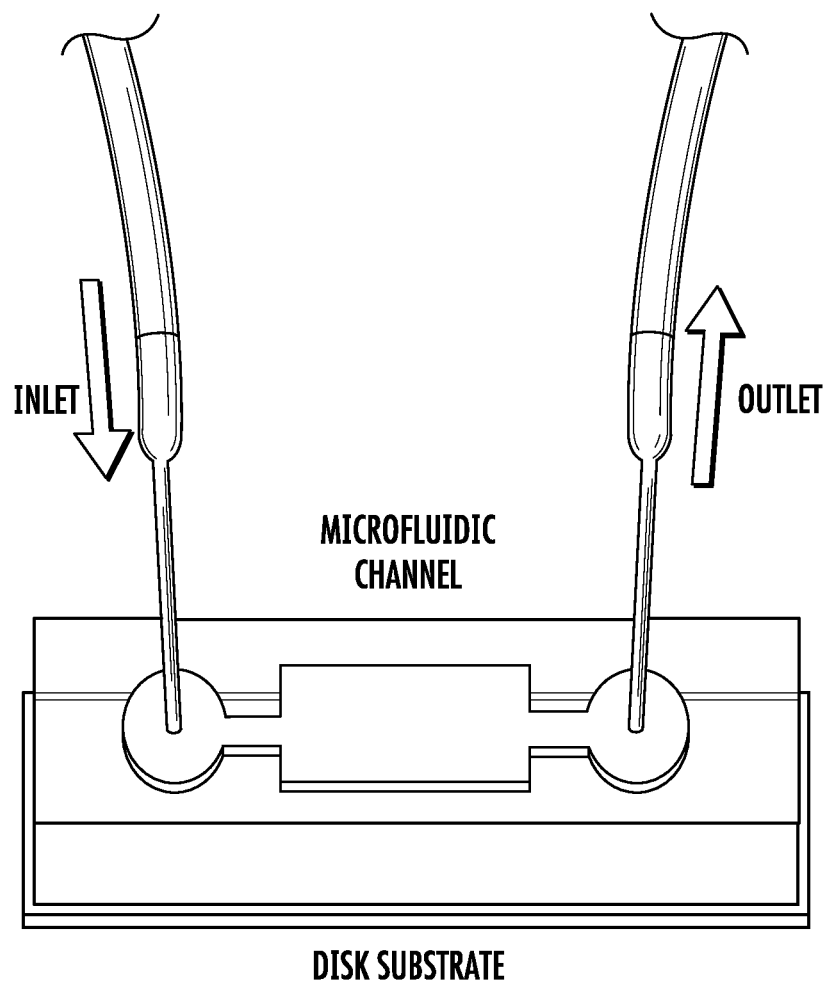
FIG. 4C is a diagram illustrating an on-chip sensor according to an embodiment.

FIG. 4 is a diagram illustrating an example of an on-chip sensor device in which an optical active resonator and a microfluidic channel have been combined. More specifically, FIG. 4A illustrates an image of the scanning electron microscope (SEM) of a 12 μm disk resonator. FIG. 4B is a partially enlarged view of FIG. 4A and illustrates two disks and a 25 nm slot. FIG. 4C is a diagram illustrating an on-chip sensor. In this case, the fabricated disk resonator has been integrated with a micro fluid channel.

FIG. 4A illustrates a SEM image of the resonator configured with a pair of an SRSN disk having a diameter of 12 μm and a thickness of 120 nm. Such disks may be separated in parallel in the 25 nm slot as illustrated in the enlarged SEM image of FIG. 4B. It was found that 8.6% of total energy in the basic mode was limited to the slot in an environment (n=1.33) in the water of FIG. 4B based on numerical analysis using COMSOL multi-physics. Accordingly, selectively sensitivity was improved 5 times with respect to an event occurred in the slot. The fabricated resonator is located in a polydimetylsiloxane (PDMS) microfluidic channel having a height of 270 μm, a width of 3 mm, and a length of 8 mm as illustrated in FIG. 4C, and may be prepared using the existing soft lithography scheme.

Figure 5:
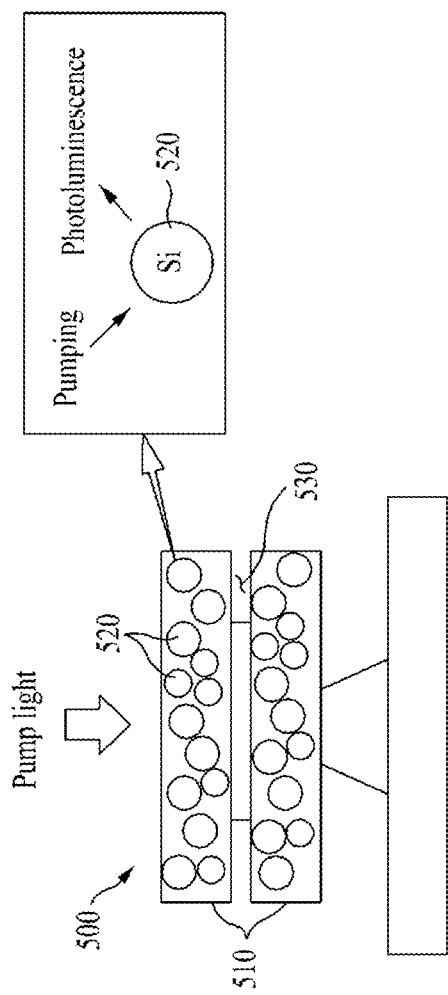
FIG. 5 is a diagram for describing an optical active resonator according to an embodiment.

FIG. 5 is a diagram for describing an optical active resonator according to an embodiment.

Referring to FIG. 5, the optical active resonator 500 according to an embodiment may include silicon nitride disk plates 510 and silicon nano-clusters 520, and may further include a nano-slot 530.

One or more silicon nitride disk plates 510 may be configured. Particularly, a plurality of silicon nitride disk plates 510 may be spaced apart from each other at a given interval.

The silicon nano-clusters 520 may be formed within the silicon nitride disk plates 510. Such silicon nano-clusters 520 may be formed by depositing an SRSN material on the silicon nitride disk plate 510 through a semiconductor process and heating the SRSN material. In this case, efficient PL can be emitted through absorption cross sections of the silicon nano-clusters 520 by only top pump beam radiation.

In other words, the silicon nano-clusters 520, that is, efficient active media, may be introduced into the optical active resonator 500. After the SRSN material is deposited through a semiconductor process, the silicon nano-cluster 520 may be formed by heating the SRSN material at a high temperature (e.g., 1200° C.).

The nano-slot 530 may be formed by disposing a plurality of the silicon nitride disk plates 510 so that they are spaced apart from each other at a given interval. For example, two silicon nitride disk plates 510 may be disposed in a nanoscale distance in parallel to form the nano-slot 530. The nano-slot 530 can focus a resonance mode within the optical active resonator 500, and may be filled with a medium including a material to be detected, which has a lower refractive index than the silicon nitride disk plate 510.

As described above, two silicon nitride disk plates 510 are disposed to overlap with a gap therebetween. Light and a material to be measured can interact with each other within the gap. At this time, light can be absorbed and emitted without a physical contact. The optical active resonator may operate in the water by controlling the size. Accordingly, emission efficiency of the optical active resonator can be further improved by optimizing the size.

In other words, a resonance mode of the optical active resonator can be focused on the nano-gap by introducing the nano-gap having a nanometer scale into an optical device. The nano-gap having several tens of nanometers may be formed within the optical active resonator so that a resonance mode within the optical active resonator is focused on the nano-gap. The results of numerical calculation based on the fabricated structure showed that strong light was focused on the nano-gap.

Accordingly, PL can be emitted by only the top pump beam radiation of a laser light source through absorption cross sections of the silicon nano-clusters 520. Moreover, PL can be emitted by only the top pump beam radiation of a single LED through absorption cross sections of the silicon nano-clusters 520 in addition to the laser light source.

The optical active resonator 500 fabricated as described above can be easily combined with a microfluidic channel and can provide an on-chip sensor not having labeling. That is, an on-chip high-sensitivity optical active resonator 500 combined with the microfluidic channel can be provided.

The fabricated optical active resonator 500 can be easily combined with the microfluidic channel and developed as an on-chip platform. Such an on-chip platform may also be developed as a cheap light source-based sensor platform, such as a single LED, in addition to a laser light source.

In general, the intensity of an LED is sufficient to excite the WGM of a resonator in a water-soluble environment (in the water), and generates a resonant peak of a PL emission spectrum. Since the emission region of the LED is much greater than that of the resonator, an LED module has only to be positioned at the top of the microfluid chip. Accordingly, measurement setup can be simplified because additional elements, such as a beam splitter, an object lens, and a CCD necessary for the concentrated and precise arrangement of a pump laser and a laser beam, are not necessary.

By introducing the silicon nano-clusters, that is, an efficient active medium, into the optical active resonator as described above, a physical contact between a device and an optical part is not necessary and a remote manipulation is possible. Accordingly, single chip coupling with additional elements essential for actual applications, such as a microfluidic channel, is possible because a remote manipulation is possible. Furthermore, although a single LED is used as a light source in addition to a common laser, the excitation and PL of the optical active resonator can be measured. In this case, the LED-based platform does not require all of a lens, light distributor, and microscope for focusing and aligning laser light in an element on a chip having a micrometer side in addition to advantages in terms of the price. As a result, a driving system for detection can be implemented very cheaply and simply. Accordingly, the optical active resonator can be used for actual clinical experiments not laboratory environment and can be easily used by anyone in addition to a skilled person.

Furthermore, light can be concentrated on the nano-gap by introducing the nano-gap having a nanometer scale into the optical device. Very high detection sensitivity compared to the existing resonance mode element within the nano-gap strongly focused on a subject can be secured. For example, upon streptavidin detection, sensitivity is 0.012 nm/nM. This is 20 times higher than the sensitivity of the existing optical active resonator-based sensor.

Figure 6:
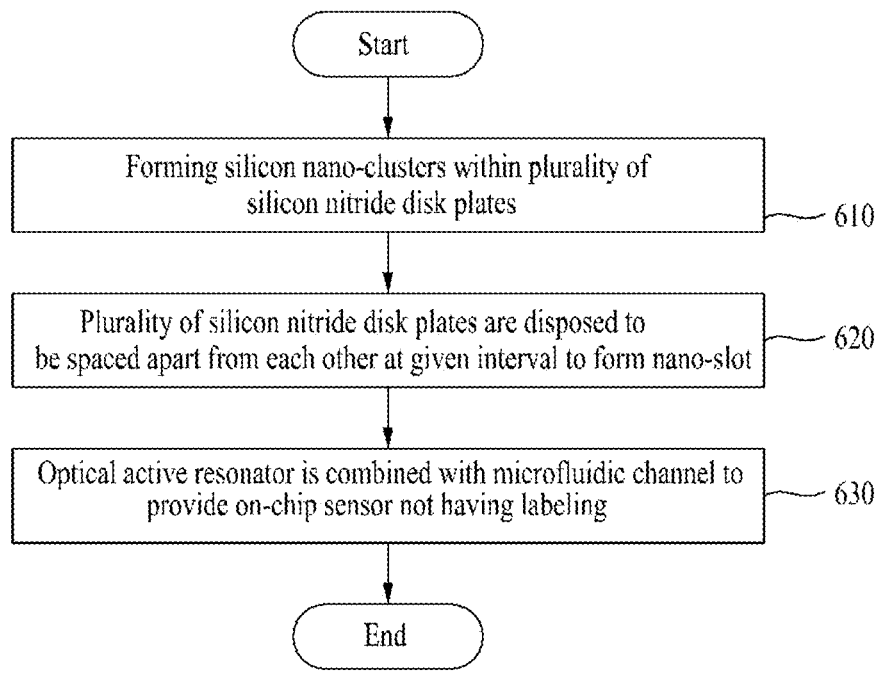
FIG. 6 is a flowchart illustrating a method of fabricating the optical active resonator according to an embodiment.

FIG. 6 is a flowchart illustrating a method of fabricating the optical active resonator according to an embodiment.

Referring to FIG. 6, the method of fabricating an optical active resonator according to an embodiment may include the step 610 of forming silicon nano-clusters within a plurality of silicon nitride disk plates and a step 620 in which the plurality of silicon nitride disk plates is spaced apart from each other at a given interval to form a nano-slot. Photoluminescence (PL) may be emitted by only top pump beam radiation through absorption cross sections of the silicon nano-clusters. Furthermore, in some embodiments, the method may further include a step 630 in which the optical active resonator is combined with a microfluidic channel to provide an on-chip sensor not having labeling.

At step 610, silicon nano-clusters may be formed within a plurality of silicon nitride disk plates. In this case, the silicon nano-clusters may be formed by depositing an SRSN material on the silicon nitride disk plates through a semiconductor process and the heating the SRSN material.

At step 620, the plurality of silicon nitride disk plates may be spaced apart from each other at a given interval to form a nano-slot. The nano-slot can focus a resonance mode within the optical resonator, and may be filled with a medium including a material to be detected, which has a lower refractive index than the silicon nitride disk plates. Accordingly, PL can be emitted by only the top pump beam radiation of a single LED in addition to a laser light source through absorption cross sections of the silicon nano-clusters.

At step 630, the optical active resonator may be combined with a microfluidic channel to provide an on-chip sensor not having labeling.

A tapered fiber is an element widely used for the signal reading of a WGM resonator sensor based on phase matching evanescent coupling. In order to overcome a fundamental limit caused by the element, an active WGM resonator may be added to a silicon nitride resonator into which the silicon nano-clusters emitting strong light have been inserted in a 700 nm wavelength range in which absorption by water is maintained low. In this case, efficient absorption of pump lighting is enabled even through an upper lighting method not through a cavity mode through very large absorption cross section of the silicon nano-clusters.

In this case, light can be emitted to the top of the optical active resonator through the transparent wall of a fusion channel by a simple free space optical device instead of a tapered fiber. Furthermore, in the optical active resonator geometry, a nano-slot structure in which two pieces of silicon nitride disk plates are disposed in parallel in a nanoscale distance may be introduced. In these experiments, the nano-slot is filled with a medium including a material to be detected, which has a lower refractive index (n=1:33) than a silicon nitride (n=2) disk plate. Due to a continuous requirement for an electrical displacement field at the interface, the great refractive index in the nanometer size dimension causes a strong constraint to the field intensity within the nano-slot, which can improve a light material interaction and corresponding sensitivity as described above.

A process of fabricating an actual device may be started by depositing an SRSN film on a silicon substrate through ion beam sputtering whose silicon concentration is controlled by a nitrogen gas. Excess silicon may be changed into silicon nano-clusters by a post-annealing process performed in an argon environment. Such a film preparation condition has been optimized to achieve maximum PL intensity using an Ar pump laser of 20 W/cm$^2$ in a 457.9 nm wavelength. In order to form a slot structure, a silicon dioxide film was deposited by an ion beam between the SRSN film deposits. The disk pattern of a photoresist defined by the existing photolithography along with a contact aligner may be delivered to a hard mask layer of amorphous silicon by the first reactive ion etching (RIE), and may be delivered to an accumulated multi-layer film by the second RIE. The amorphous silicon hard mask may be removed by wet etch in a KOH solution, which is performed to undercut silicon at the bottom of the resonator structure. Finally, the silicon dioxide film may be etched by a buffered oxidation etchant to form a nano-slot between the SRSN disks. A device design and fabrication condition can be finely optimized to obtain a high quality coefficient of the optical active resonator under a water-soluble environment essential for measurement in a microfluidic channel using top pumping.

Optical setup for fraction bound measurement and actual optical signal measurement are described below.

One embodiment can provide a high-sensitivity SRSN microcavity sensor in a simple and practical form, which has been integrated with a microfluidic channel, by increasing the quality coefficient of a PL emission and water-soluble environment. In the SRSN microcavity, the excitation of a WGM can be measured by a spectrometer through free space optics without an optical component for a direct physical contact. An interaction between light and a material can be increased and sensitivity can be increased by embedding, in the microcavity, a nano-slot structure on which a mode field has been focused and in which biomolecular detection is performed. The molecular detection action was proved through a streptavidin-biotin complex. This shows that device sensitivity was 0.012 nm/nM and an association rate based on real-time bonding was analyzed as $3\times10^{-4}M^{-1}s^{-1}$ using the Langmuir model. A substantial method of determining an unknown concentration of a material to be analyzed through one measurement by analyzing the equation of a fraction used in molecular dynamics quantization is proposed and experimentally proved. Furthermore, the WGM is configured in the optical active resonator using an LED pump source for focusing and aligning a laser beam on the optical active resonator by excluding an expensive laser pump source and an optical component from the measurement setup for the first time. Such a simple LED-based detection platform may be applied to refractive detection for glycerol diluted in water, causing sensitivity of 226.67 nm/refractive index unit (RIU).

An interaction between streptavidin and biotin may be measured. Performance of a developed microfluid WGM resonator sensor was verified below by the real-time measurement of a bio-molecule interaction based on a streptavidin-biotin complex whose noncovalent bond is significantly strong. Prior to experiments, the SRSN resonator may be pre-processed using biotin. When streptavidin of a DPBS flows into a fluid channel, streptavidin starts to attach biotin on a surface of the optical active resonator. Streptavidin that has closely attached biotin on the surface of the resonator may increase the length of an optical path of a resonance mode. Accordingly, a resonance movement may occur because the resonance state of the optical active resonator is changed.

Figure 7:
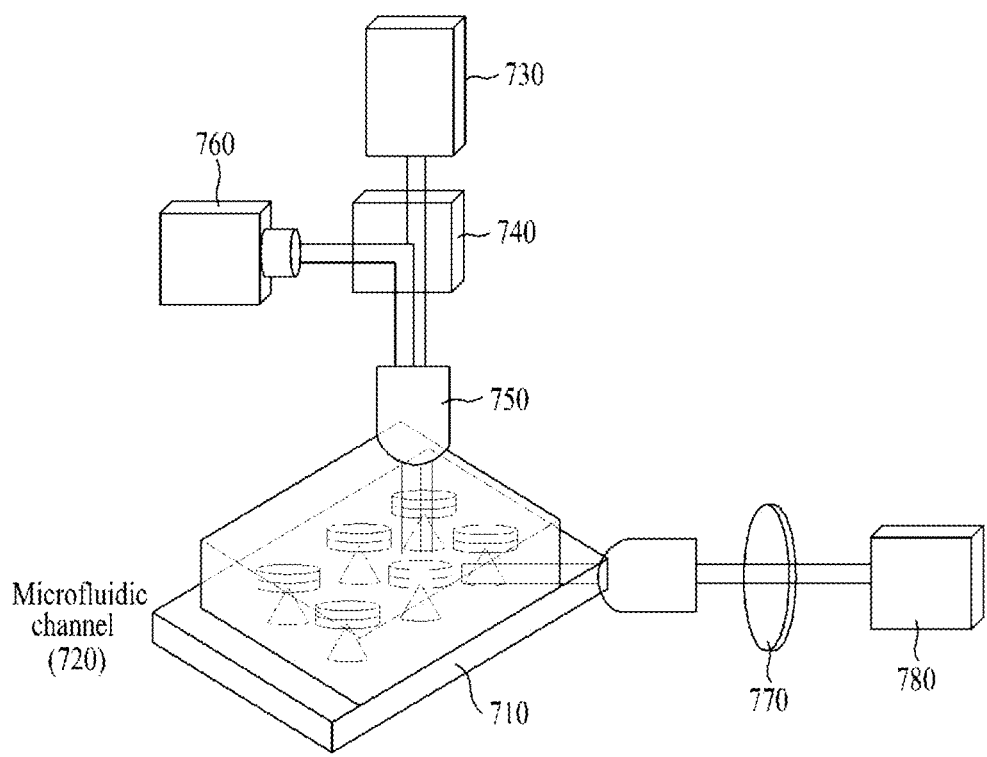
FIG. 7 is a diagram for describing a laser pump-based optical active resonator according to an embodiment.

FIG. 7 is a diagram for describing a laser pump-based optical active resonator according to an embodiment.

FIG. 7 illustrates the state in which experiments for measuring a resonant frequency movement in real time using the optical active resonator described with reference to FIG. 5 according to an embodiment have been set up. A laser light source may be used as a light source. That is, FIG. 7 illustrates an optical setup method and actual setup state for fraction bound measurement based on a photodetector.

A beam of a 457.9 nm wavelength argon laser 730 may be concentrated on the top of an SRSN resonator 710 through the PDMS wall of a micro microfluidic channel 720. The laser intensity of a focal plane is 20 W/cm$^2$ and may obtain strong PL emission including a characteristic cavity mode profile by stimulating silicon nano-clusters. The PL emission is collected through the side wall of the microfluidic channel 720 by an objective lens 750 (numerical aperture: 0.15). In this case, a transverse magnetic (TM) polarization component may be selectively captured by a polarity bond. Real-time frequency spectra that have reached a spectrometer 780 may show the respective measured TM modes of the SRSN WGM resonator as in FIGS. 9A and 9B. The TM mode may be selectively measured as a cavity TM mode because the TM mode has a slot structure and can be firmly fixed compared to a TE mode. In this case, a beam splitter 740 may be configured between the argon laser 730 and the objective lens 750 and between the objective lens 750 and a CCD camera 760. A separate objective lens, a polarizer 770 and the spectrometer 780 may be configured for measurement.

Figure 8:
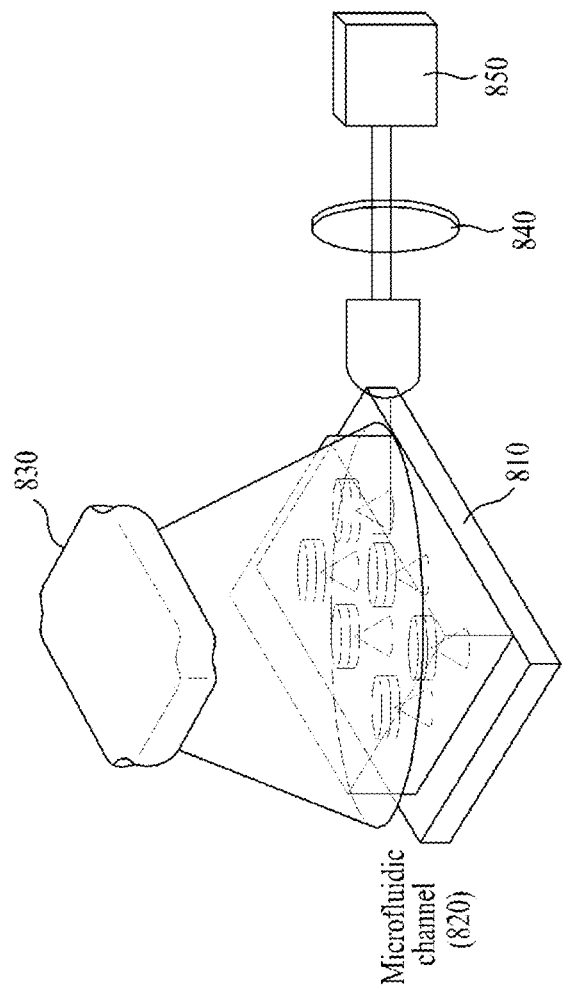
FIG. 8 is a diagram for describing an LED pump-based optical active resonator according to an embodiment.

FIG. 8 is a diagram for describing an LED pump-based optical active resonator according to an embodiment.

FIG. 8 illustrates the state in which experiments for measuring a resonant frequency movement in real time using the optical active resonator described with reference to FIG. 5 according to an embodiment have been set up. An LED laser light source may be used as a light source.

As described with reference to FIG. 7, a beam of an LED light source 830 may be concentrated on the top of an SRSN resonator 810 through the PDMS wall of a microfluidic channel 820. A separate objective lens, a polarizer 840 and a spectrometer 850 may be configured for measurement.

FIG. 9 is a diagram illustrating TM modes of the SRSN WGM resonator measured using the spectrometer according to an embodiment.

Figure 9A:
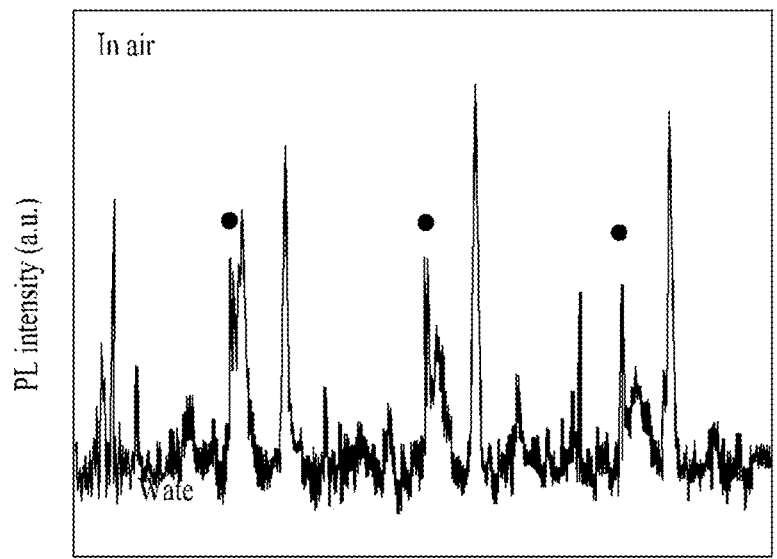
FIG. 9A illustrates resonance modes measured by the photodetector according to an embodiment.
Figure 9B:
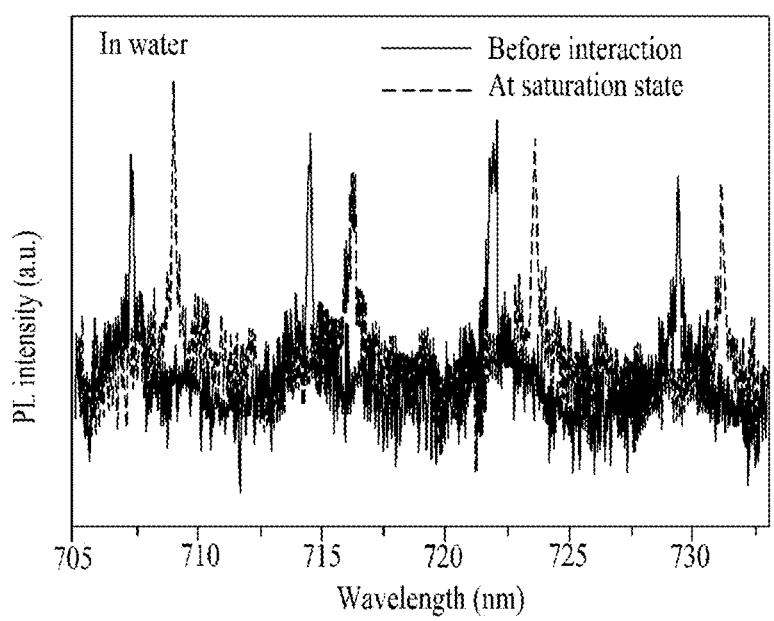
FIG. 9B illustrates shifts of resonance modes attributable to a reaction between a subject and a ligand according to an embodiment.

FIG. 9A illustrates resonance modes measured by the photodetector. Each of basic mode families that belong to many resonance modes illustrated in FIG. 9A and that are indicated by dots may be distinguished from a high-level mode by comparing the measured free spectral range (FSR) of each mode family with a value estimated by numerical analysis. The FSR of a TM basic mode is 7.9 nm and greater than 15,000 calculated in the full width half maximum (FWHM) of a measured PL peak, which corresponds to the resolution limit of the spectrometer. FIG. 9B illustrates shifts of resonance modes attributable to a reaction between a subject and a ligand. A fraction bound may be measured using such a shift. The high-level mode disappears in a PL spectrum measured in a water-soluble environment of FIG. 9B. The reason for this is that if a refractive index between the resonator structure and the environment is reduced, a higher level mode and a resonator diameter so that a severe and additional emission loss can be caused selectively (not a basic mode) are carefully selected. Such a clear spectrum facilitates analysis because it prevents an overlap between other modes. In FIG. 9B, the FSR of the mode is 7.2 nm and is well matched with the FSR of the basic mode in the water-soluble environment estimated by number analysis. A mode Q coefficient in the water-soluble condition is about 8,500 and 0.08 nm calculated in the FWHM of a PL peak.

FIG. 9B illustrates resonant frequency movements attributable to a bonding event of streptavidin for surface-processed biotin in the form of PL spectra before and after streptavidin having a 144 nM concentration. The PL spectrum is measured after the state of a frequency movement is a saturation state. In FIG. 9B, a peak shift of 1.72 nm may provide sensitivity of 0.012 nm/nM. A resolution limit defined by the FWHM of a resonance mode is about 0.08 nm, and a detection limit of the device is proved as 6.7 nM in the case of streptavidin. The sensitivity of the device according to embodiments is 22 times higher than the sensitivity of an active WGM sensor not having direct physical coupling, which was reported before.

The measurement of a fraction bound measured by the fabricated optical sensor, and optical setup and actual optical signal measurement for a method of determining a concentration are described below. FIGS. 10A to 10D are diagram illustrating the real-time peak shifts of resonant wavelengths of a material to be detected according to an embodiment.

Figure 10A:
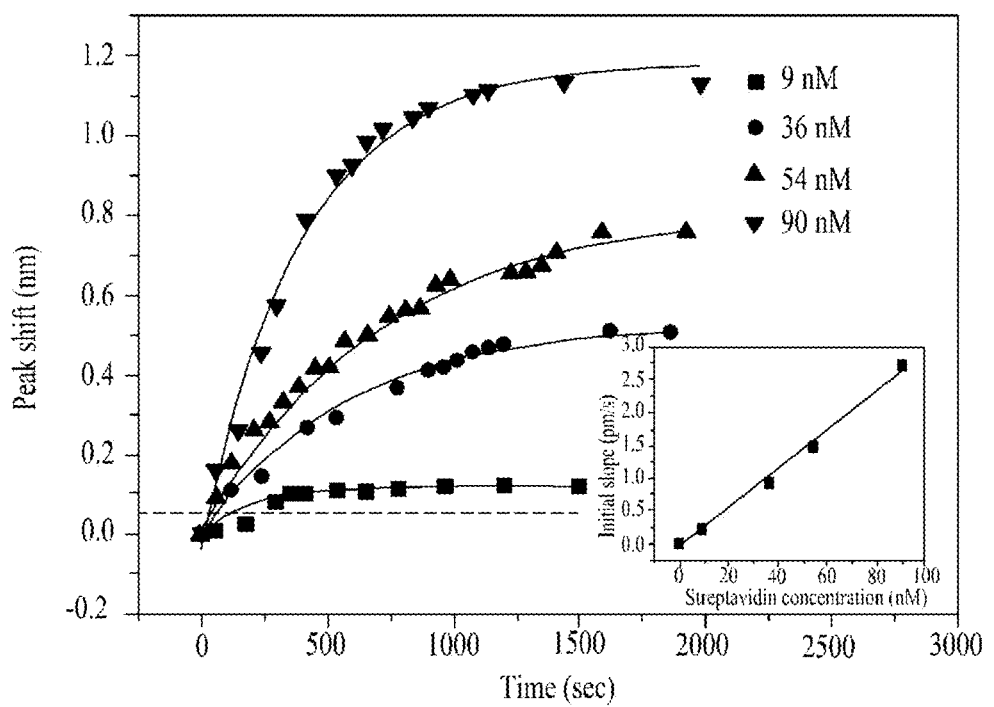
FIG. 10A illustrates fraction bounds of actual measured streptavidin for each concentration according to an embodiment.

In order to additionally research the developed detection device and to analyze the influence of the nano-slot structure on molecule dynamics, a time-excessive operation of a frequency movement caused by an interaction was measured. FIG. 10A illustrates fraction bounds of actual measured streptavidin for each concentration, and illustrates real-time peak shifts of resonant wavelengths continuously measured at intervals of several minutes after four types of concentrations (e.g., 9 nM, 36 nM, 54 nM, and 90 nM) of streptavidin diluted in the DPBS medium were injected into the microfluidic channel. Such a time shift of the frequency movement may be understood based on the Langmuir model. This is commonly used to analyze the kinetics of a surface bonding reaction in a system in which a ligand has been fixed to a firm surface. A fraction proportional to a bio sensor signal may be defined as the number of ligands and analysis complexes based on the Langmuir model, and may be divided by a total number of ligands represent in the following equation in a connection step.

$$fb(t, c) = fbeq(c) \times [1 - \exp(k_{on}^{obs} \times t)] \quad (7)$$

$$fbeq(c) = \frac{c}{c + K_d} \quad (8)$$

$$k_{on}^{obs} = c \times k_{on} + k_{off} \quad (9)$$

In Equation 7, $k_{on}^{obs}$ is a rate constant which may be observed based on an internal combustion relation ratio "kon" and dissociation rate "koff" in addition to "c." In [Equation 8], fbeq(c) is an equilibrium fraction, c is the concentration of an analysis material, and Kd is a differentiation constant and defined as $$\frac{koff}{kon}$$

in the saturation state. In FIG. 10A, a solid line indicates a suitable curve of Equation 7 for measured data points. In this curve, values of $k_{on}^{obs}$ and fbeq(c) can be obtained. Kd, kon and koff can be derived by substituting the two values with Equation 8 and Equation 9 and solving both the equations at the same time. Association rates obtained from the suitable curve are $1.2 \times 10^4$ $M^{-1}$ $s^{-1}$, $4.2 \times 10^3$ $M^{-1}$ $s^{-1}$, $3.2 \times 10^3$ $M^{-1}$ $s^{-1}$, and $6.4 \times 10^3$ $M^{-1}$ $s^{-1}$ with respect to streptavidin concentrations of 9 nM, 36 nM, 54 nM, and 90 nM, respectively. These are quite matched with the previously reported association rates. A slightly higher association rate of 9 nM streptavidin occurs due to the detection limit of the 0.05 nm (FIG. 10A) spectrometer. This is not sufficient for accurate measurement of a frequency movement attributable to the kinetics of a low concentration. As control experiments, Bovine Serum Albumin (BAS) also flows into the microfluidic channel for 35 minutes through the WGM resonator into which biotin has been processed. The BSA is not specially combined with biotin. Accordingly, the BSA induces a much lower frequency movement of 0.25 nm in 1 mg/mL, that is, a concentration several hundreds of times higher than that of streptavidin used in the experiments.

In a mass-transport restriction condition occurring in molecule kinetics analysis in common, an initial slope in the association step is linearly proportional to the concentration of the analysis material according to the first rule of Fick. Such a trend evidently appears on the inside of FIG. 10A. In this case, a point indicates an initial slope in the association step for each concentration. A line indicates a linear suitable value of a data point at which the slope corresponds to the association rate "kon."

Figure 10B:
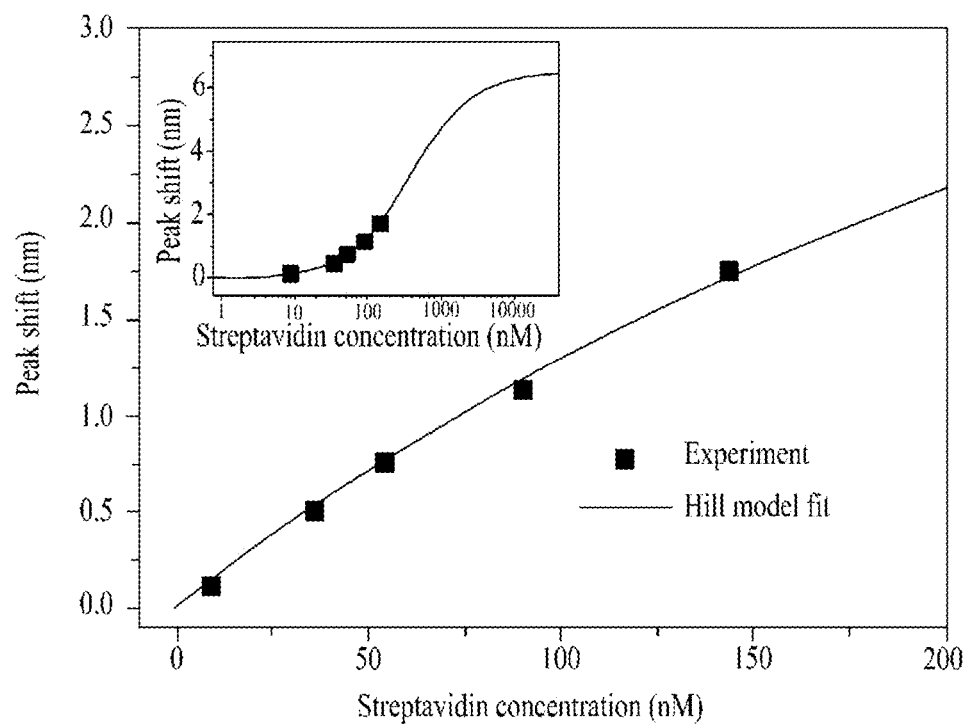
FIG. 10B illustrates fraction bounds for each concentration in the saturation state of the reaction according to an embodiment.

In FIG. 10A, at the final timing, a streptavidin and biotin reaction enters the saturation state. In the saturation state, a frequency movement is analyzed in detail in FIG. 10B. FIG. 10B illustrates fraction bounds for each concentration in the saturation state of the reaction. A square point indicates a frequency movement in the saturation state according to a streptavidin concentration, and the square points are combined by Equation 8 called a Hill model function indicated by a line. In FIG. 10B, an x axis indicates a linear scale. A figure within FIG. 10B illustrates the log scale of the same data. From the drawings, it was experimentally proved that Kd and koff of the streptavidin-biotin complex are $3.8 \times 10^{-7}$ M (dotted line in FIG. 10B) and $1.4 \times 10^{-2}$ s$^{-1}$, respectively, and are well matched with the previous report based on the function of fbeq(c).

In general, in the case of analysis on the dynamics of molecules, serial signals need to be measured for several seconds at a reaction start point as in FIG. 10A. However, it is necessary to rapidly measure the concentration of a target analysis material within a sample rather than to sufficiently analyze the dynamics of molecules. Accordingly, an efficient method of calculating a relative concentration of the analysis material through one measurement at a time is simulated regardless of timing at which a relative concentration of the analysis material is measured. A unique peak shift ratio R(t), that is, the ratio of peak changes of two different samples, may be defined using the association step of Equation 7. In this case, one sample is an analysis target, and the other sample is a reference whose analysis material concentration has already been known. That is, R(t) is defined as $$\frac{fb(0, C_{sample})}{fb(0, C_{reference})}.$$

In an initial condition, R(t) corresponds to $$\frac{fb'(0, C_{sample})}{fb'(0, C_{reference})}.$$

This results in $$\frac{C_{sample}}{C_{reference}},$$

that is, the ratio of the original concentration. In a full saturation state, R(t) may be arranged as $$\frac{C_{sample} \times (C_{reference} + Kd)}{C_{reference} \times (C_{sample} + Kd)}.$$

Figure 10C:
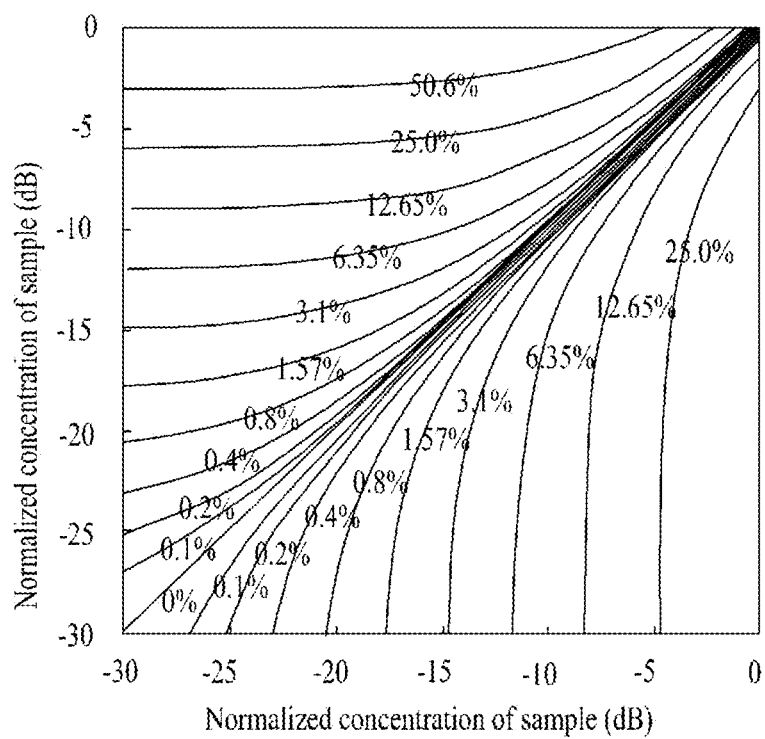
FIG. 10C illustrates an error rate graph of concentrations determines in the method of measuring a concentration based on the ratio of the reference signal and the sample signal according to an embodiment.

In a transition period, R(t) is a monotone function, and thus the R(t) value is located between an initial value and a saturation value. That is, the error rate of R(t) according to the ratio of the original concentration defined as $$\left| R(t) - \frac{C_{sample}}{C_{reference}} \right| \times \frac{C_{sample}}{C_{reference}} \times 100$$

is 0 in the initial state, and monotonically increases up to $$\frac{C_{sample} \times (C_{reference} + Kd)}{C_{reference} \times (C_{sample} + Kd)},$$

that is, a maximum value occurring in the full saturation state. A relative peak shift compared with the reference based on the calculation is measured to prove that the concentration of the analysis material is determined as a constant error rate or less. A maximum error rate obtained using such a method is the function of an analysis material concentration. Accordingly, maximum error rates for the normalized concentrations of the sample and the reference defined as $$\frac{C_{sample}}{Kd} \text{ and } \frac{C_{reference}}{Kd}$$

are illustrated in FIG. 10C. That is, FIG. 10C illustrates an error rate graph of concentrations determines in the method of measuring a concentration based on the ratio of the reference signal and the sample signal. In FIG. 10C, as a maximum error rate increases based on the normalized concentration, information on a maximum concentration equal to or lower than a value on which an unknown concentration can be measured with higher accuracy than a specific error rate can be obtained. For example, if the standardized concentration of the reference is fixed to 10% of Kd, a concentration of an unknown analysis material less than 22% of Kd can be measured at an error rate of less than 10% through one measurement at any timing.

Figure 10D:
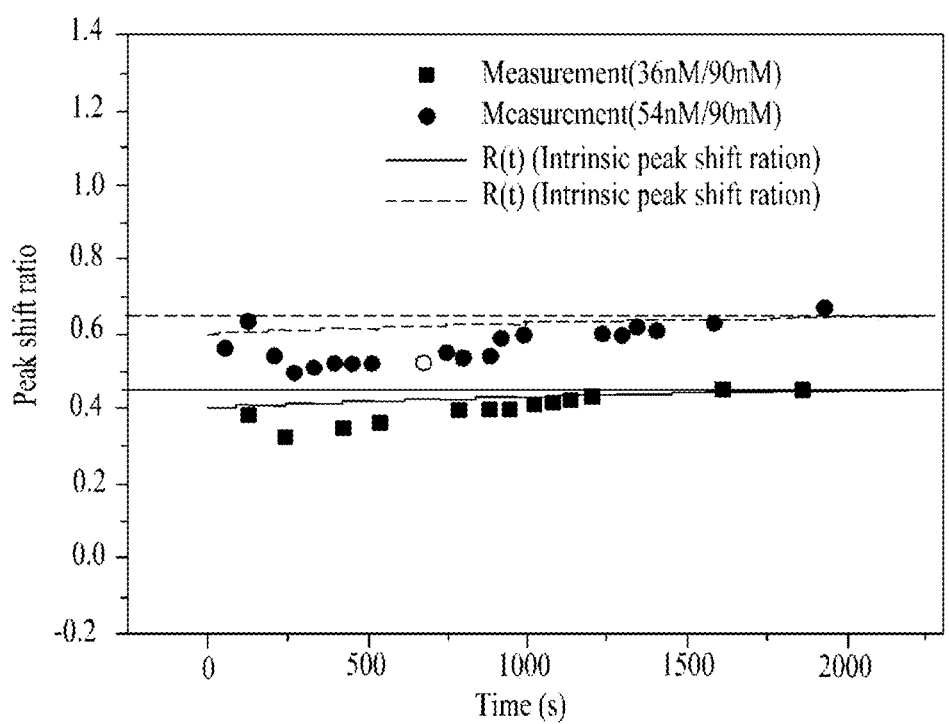
FIG. 10D illustrates that a method of measuring a concentration based on the ratio of a reference signal and a sample signal has been applied to actual experiments according to an embodiment.

The method proposed as described above was applied to experiment results, which proved the accuracy of FIG. 10D. A sample, that is, a reference, had a concentration of 90 nM, and the analysis material had a concentration of 36 nM and 54 nM. The ratio of streptavidin concentrations corresponds to 0.4 in the case of 36 nM and 0.6 in the case of 54 nM, which are based on a concentration reference of 90 nM. A unique peak shift ratio for each sample is indicated. This shows that an initial value is perfectly matched with the ratio of the original concentration and the error rate monotonously increases up to a maximum value of the calculated saturation state. FIG. 10D illustrates that a method of measuring a concentration based on the ratio of a reference signal and a sample signal has been applied to actual experiments. In FIG. 10D, circles and squares indicate peak shift ratios based on the real-time measurement data of FIG. 10A and are matched with a solid-line trend. In this case, a point indicates an experiments value, and a line indicates a calculated value. Average error rates of measurement data having concentration ratios of 0.4 and 0.6 are 4.2% and 10.9%, respectively. Such an experiment value is very close to a maximum error rate of a normalized concentration indicated by the dots in FIG. 10C. In the initial measurement period, a relatively great deviation occurs between measurements and a unique peak shift ratio chiefly due to the inaccuracy of peak shift measurement attributable to a quantized error according to the resolution limit of the spectrometer.

Figure 11:
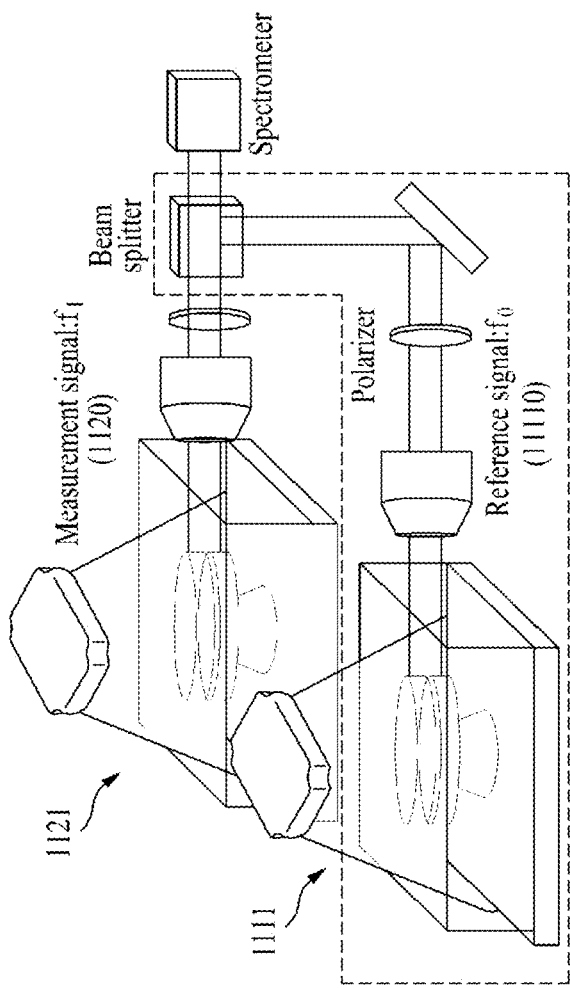
FIG. 11 is a diagram for describing the configuration of a top pump configuration including an LED according to an embodiment.

FIG. 11 is a diagram for describing the configuration of a top pump configuration including an LED according to an embodiment.

As illustrated in FIG. 11, an argon laser, that is, the pump supply source of the SRSN resonator may be substituted with a commercialized high-intensity LED that emits light in an absorption wavelength of the silicon nano-clusters due to the high absorption cross sections of the silicon nano-clusters. 18 LEDs having a center wavelength 365 nm (LUMINUS SST10-UV) may be used in the top pump source because the silicon nano-clusters more efficiently absorb UV than a visible ray. If absorption by a fluid channel PDMS wall is neglected, valid intensity of an LED assembly part on a surface of the resonator chip spaced apart from the LED by 4 mm is about 5.6 W/cm². The intensity of the LED is smaller than that (20 W/cm²) of the argon laser, but is sufficient to excite the WGM of the resonator in a water-soluble environment, so a resonant peak of an emission spectrum is generated. Since the emission region of the LED is much greater than that of the resonator, the LED is sufficient for arrangement if the LED module has only to be positioned at the top of the microfluid chip. Accordingly, measurement setup can be simplified as indicated outside a dotted line in FIG. 11 because additional elements, such as a beam splitter, an object lens and a CCD that require the intensive and precise arrangement of a pump laser and laser beam, are not necessary.

Figure 12:
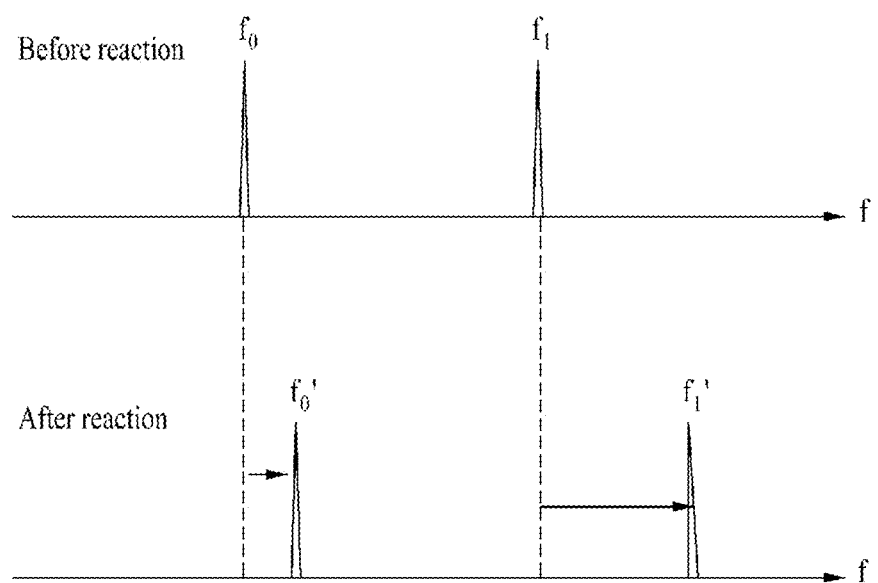
FIG. 12 is a diagram illustrating signals measured by the spectrometer according to an embodiment.

FIG. 12 is a diagram illustrating signals measured by the spectrometer according to an embodiment.

FIG. 12 illustrates the measured signals of the spectrometer before and after a reaction in a simultaneous measurement platform, such as that illustrated in FIG. 11, and may be represented as in the following equation.

$$\frac{f_1 - f_1'}{f_0 - f_0'} = \frac{c_1}{c_0} \frac{\text{concentration of sample to be determined}}{\text{concentration of reference sample}} \quad (10)$$

If $f_0$, that is, a reference signal, and $f_1$, that is, a sample signal, are measured at the same time regardless of reaction timing, a concentration of a sample can be determined through accurate measurement in the state in which external change factors have been offset.

Figure 13A:
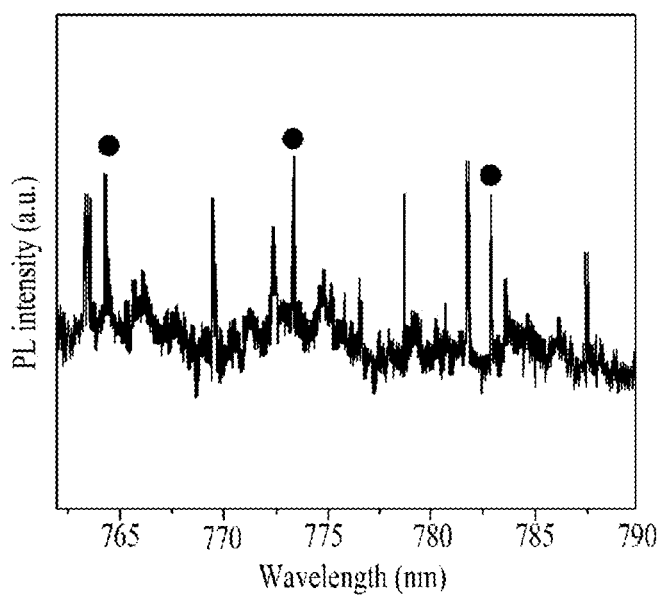
FIG. 13A illustrates the PL spectrum of the SRSN resonator pumped by a single LED in an air environment according to an embodiment.
Figure 13B:
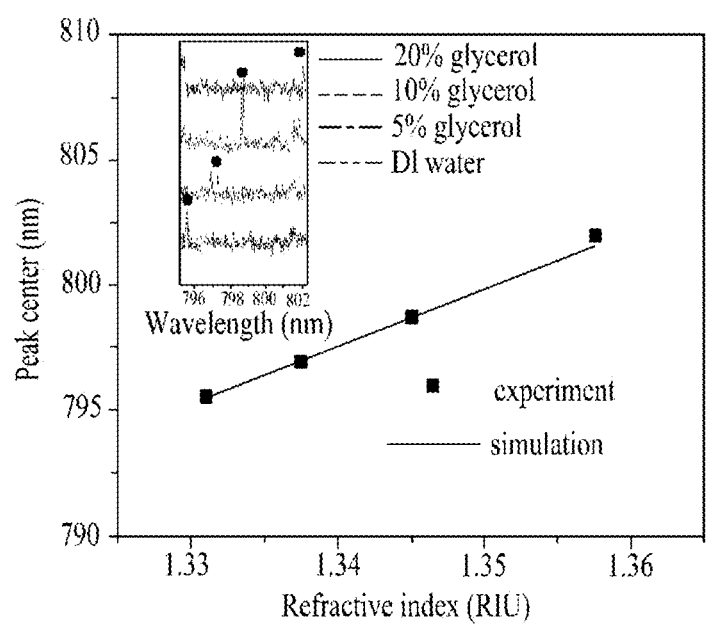
FIG. 13B illustrates resonant frequencies of the SRSN resonator when glycerol diluted at the three different concentrations was serially injected into the microfluidic channel according to an embodiment.

FIGS. 13A and 13B is a diagram illustrating a PL spectrum of the SRSN resonator and resonant frequencies of the SRSN resonator using the top pump including an LED according to an embodiment.

FIG. 13A illustrates the PL spectrum of the SRSN resonator pumped by a single LED in an air environment. The FSR and quality coefficient of a TM basic mode are precisely the same as values (9.1 nm and 15,000, respectively) of an argon laser pump. In order to check a proper operation of the LED-pumped configuration suitable for detection use, mass-detection experiments were performed in which a concentration of a target chemical material uniformly distributed to a medium could be measured by detecting a change in the refractive index. Glycerol was diluted at three concentrations of 5%, 10% and 20% in DI (ionization) water. The refractive indices of the mixed medium were 1.338, 1.345 and 1.359, respectively, in the DI water 1.331.

A figure within FIG. 13B illustrates resonant frequencies of the SRSN resonator when glycerol diluted at the three different concentrations was serially injected into the microfluidic channel. Measured wavelengths of resonance are very similar to linear frequency movements of 226.67 nm/RIU that are numerically estimated in COMSOL multiphysics with respect to the TM basic mode indicated in FIG. 13B. When a resolution limit value of 0.08 nm defined by the FWHM of a resonance mode is considered, the limit of detection for a change of the glycerol concentration is about 0.25%.

In this case, an optically active SRSN resonator sensor integrated with the microfluidic channel has been developed in a practical form free from the existing strict severe connection method dependent on a tapered fiber. The sensitivity of the device checked through the real-time measurement of the streptavidin-biotin complex was 0.012 nm/nM, which is 20 times or high compared to the previously reported active WGM sensor not having a physical and direct coupling. As a result, it could be seen that the nano-slot structure of a 25 nm slot introduced to increase sensitivity does not greatly change a molecule dynamic relation because characteristic parameters, such as kon, koff, and Kd, are identified to be the same as the previously reported values.

Furthermore, the detection of a WGM based on the direct light of an LED pump has been proved for the first time using great absorption cross sections of the silicon nano-clusters. Since the successful proof of the detection of the refractive system dependents on the 365 nm LED pump, bio molecules deformed in ultraviolet rays are not compatible with a current LED-based measurement platform. Accordingly, there is a need for additional research for improving efficiency of an SRSN resonator suitable for pumping using a visible LED source that has relatively low intensity, but does not deform biomolecules.

Furthermore, there has been proposed the fast and efficient method capable of calculating a concentration of an analysis material through one measurement at a time based on a relative peak shift for a reference sample. If the method is combined with the LED-based platform, peak shifts of a sample and reference sample can be measured at the same time in single measurement setup as in FIG. 11. This means that a change in the resonant frequency caused by external factors that uniformly affect the resonator, such as a temperature change and a surface pre-processing condition, can be automatically offset by a noise offset operation of balanced detection. In this case, it is expected that the approach method can open a road on which a cost-efficient on-chip (not having labeling) sensor can be implemented for practical applications capable of operating by single measurement setup for use convenience.

The aforementioned apparatus may be implemented in the form of a hardware component, a software component or a combination of a hardware component and a software component. For example, the apparatus and components described in the embodiments may be implemented using one or more general-purpose computers or special-purpose computers, like a processor, a controller, an arithmetic logic unit (ALU), a digital signal processor, a microcomputer, a field programmable array (FPA), a programmable logic unit (PLU), a microprocessor or any other device capable of executing or responding to an instruction. The processor may perform an operating system (OS) and one or more software applications executed on the OS.

Furthermore, the processor may access, store, manipulate, process and generate data in response to the execution of software. For convenience of understanding, one processing device has been illustrated as being used, but a person having ordinary skill in the art may understand that the processor may include a plurality of processing elements and/or a plurality of types of processing elements. For example, the processor may include a plurality of processors or a single processor and a single controller. Furthermore, a different processing configuration, such as a parallel processor, is also possible.

Software may include a computer program, code, an instruction or a combination of one or more of them and may configure a processor so that it operates as desired or may instruct the processor independently or collectively. The software and/or data may be embodied in a machine, component, physical device, virtual equipment or computer storage medium or device of any type in order to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure solely or in combination. The program instruction recorded on the recording medium may have been specially designed and configured for the embodiment or may have been known to those skilled in the computer software. The computer-readable recording medium includes magnetic media such as a hard disk, a floppy disk and a magnetic tape, optical media such as a CD-ROM and a DVD, magneto-optical media such as a floptical disk, and hardware devices specially configured to store and execute program instructions, such as ROM, RAM, and flash memory, for example. Examples of the program instruction may include high-level language code executable by a computer using an interpreter in addition to machine-language code, such as code written by a compiler.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and the equivalents of the claims belong to the scope of the claims.

The embodiments can provide a fast and efficient method of determining a concentration of a subject based on fraction bound measurement, which can determine a relative concentration of a sample based on a comparison with a reference signal through only one signal measurement at any reaction timing in addition to an initial stage.

Furthermore, the embodiments can provide a method of determining a concentration of a subject based on fraction bound measurement which enables accurate measurement by offsetting an external factor that may affect experiment results through the simultaneous measurement of a reference signal and a sample signal.

What is claimed is:

1. A method of determining a concentration of a subject, comprising:
    fixing a ligand to a surface of an optical device;
    measuring a fraction bound signal of the subject based on an optical signal detected when the subject reacts with the ligand fixed to the surface of the optical device, the fraction bound signal of the subject being measured at any reaction timing of an initial step, an intermediate step or a saturation step of the reaction;
    measuring a reference fraction bound signal for a reference sample with a known concentration, the reference fraction bound signal being measured at each of the initial step, the intermediate step and the saturation step of the reaction;
    calculating a ratio of the fraction bound signal of the subject measured at said any reaction timing to the reference fraction bound signal of the reference sample measured at a corresponding reaction timing; and
    determining a relative value of the concentration of the subject based on the calculated ratio
    wherein reaction of the subject with the ligand follows a Langmuir model so that the fraction bound signal ratio would be substantially constant in course of the reaction and so that the relative concentration of the subject is determined based on the calculated ratio, and said any first reaction timing is any point of time in the initial step, the intermediate step or the saturation step.

2. The method of claim 1, wherein measuring the fraction bound signal of the subject based on the optical signal comprises measuring the fraction bound signal of the subject indicative of a number of ligands combined with the subject against a total number of the ligands.

3. The method of claim 1, wherein measuring the fraction bound signal of the subject based on the optical signal comprises analyzing the fraction bound through a Langmuir model in an environment in which the ligand has been fixed to the surface of the optical device.

4. The method of claim 1, wherein in determining the relative value of the concentration of the subject, the calculated ratio is a monotone function.

5. The method of claim 1, wherein measuring the fraction bound signal of the subject based on the optical signal and the reference fraction bound signal of the reference sample are conducted simultaneously in such a way as to enable accurate measurement by offsetting external factors capable of affecting experiments.

6. The method of claim 1, wherein measuring the fraction bound signal of the subject based on the optical signal comprises simultaneously measuring signals of a plurality of samples in an identical condition in such a way as to enable accurate measurement by offsetting external factors capable of affecting experiments.

7. The method of claim 1, further comprising fabricating an optical active resonator used as the optical device in the fraction bound signal measurement,
    wherein fabricating the optical active resonator comprises:
    forming silicon nano-clusters within a plurality of silicon nitride disk plates; and
    disposing the plurality of silicon nitride disk plates in such a way as to be spaced apart from each other at a given interval to form a nano-slot, wherein photoluminescence (PL) is emitted by only top pump beam radiation through absorption cross sections of the silicon nano-clusters.

8. The method of claim 7, further comprising radiating a pump beam of a single light-emitting diode (LED) over the optical active resonator for the fraction bound measurement, wherein the PL is emitted by only the top pump beam radiation of the single LED through the absorption cross sections of the silicon nano-clusters.

* * * * *